(12) United States Patent
Antoncic et al.

(10) Patent No.: US 7,943,786 B2
(45) Date of Patent: May 17, 2011

(54) PROCESS FOR PREPARING AMORPHOUS (4R-CIS)-6-[2-[3-PHENYL-4-(PHENYLCARBAMOYL)-2-(4-FLUOROPHENYL)-5-(1-METHYLETHYL)-PYRROL-1-YL]-ETHYL]-2,2-DIMETHYL-[1,3]-DIOXANE-4-YL-ACETIC ACID

(76) Inventors: Ljubomir Antoncic, Ljubljana (SI); Gorazd Sorsak, Ljubljana (SI)

( * ) Notice: Subject to any disclaimer, the term of this patent is extended or adjusted under 35 U.S.C. 154(b) by 1052 days.

(21) Appl. No.: 10/584,638

(22) PCT Filed: Dec. 27, 2004

(86) PCT No.: PCT/SI2004/000045
§ 371 (c)(1),
(2), (4) Date: Jun. 26, 2006

(87) PCT Pub. No.: WO2005/063741
PCT Pub. Date: Jul. 14, 2005

(65) Prior Publication Data
US 2007/0179308 A1    Aug. 2, 2007

(30) Foreign Application Priority Data
Dec. 29, 2003 (SI) .................. P-200300321
Jan. 23, 2004 (SI) .................. P-200400022

(51) Int. Cl.
*C07D 405/00* (2006.01)

(52) U.S. Cl. ..................................... 548/517
(58) Field of Classification Search .............. 548/517
See application file for complete search history.

(56) References Cited

U.S. PATENT DOCUMENTS

| 5,155,251 A | 10/1992 | Butler et al. |
| 7,186,848 B2 * | 3/2007 | Barkoczy et al. ............. 548/517 |
| 2003/0109569 A1 | 6/2003 | Sorsak et al. |
| 2003/0114685 A1 | 6/2003 | Niddam-Hildesheim et al. |
| 2003/0212279 A1 | 11/2003 | Tessler et al. |
| 2004/0249168 A1 | 12/2004 | Barkoczy et al. |

FOREIGN PATENT DOCUMENTS

| EP | 0330172 | 8/1989 |
| WO | WO03/082816 | 10/2002 |

OTHER PUBLICATIONS

Baumann K L et al: "The convergent synthesis of CI-981, an optically actives, highly potent, tissue selective inhibitor of HMG-COA reductase" Tetrahedron letters, elsevier science publishers, Amsterdamn NL, vol. 33, No. 17, Apr. 21, 1992, pp. 2283-2284, example 7.

* cited by examiner

*Primary Examiner* — Rei-tsang Shiao
(74) *Attorney, Agent, or Firm* — Merchant & Gould PC

(57) ABSTRACT

The invention relates to a process of preparing amorphous (4R-cis)-6-[2-[3-phenyl-4-(phenylcarbamoyl)-2-(4-fluorophenyl)-5-(1-methylethyl)-pyrrol-1-yl]-ethyl]-2,2-dimethyl-[1,3]-dioxane-4-yl-acetic acid-tertiary butyl ester which is a useful pharmaceutical intermediate in the preparation of atorvastatin salts.

6 Claims, 2 Drawing Sheets

PROCESS FOR PREPARING AMORPHOUS (4R-CIS)-6-[2-[3-PHENYL-4-(PHENYLCARBAMOYL)-2-(4-FLUOROPHENYL)-5-(1-METHYLETHYL)-PYRROL-1-YL]-ETHYL]-2,2-DIMETHYL-[1,3]-DIOXANE-4-YL-ACETIC ACID

This application is the National Stage of International Application No. PCT/SI2004/000045, filed on Dec. 27, 2004 which claims benefit under 35 U.S.C. §119(a)-(d) or (f) of Slovenia patent application P200300321, filed on Dec. 29, 2003, and P2004400022 filed on Jan. 23, 2004; the contents of both are incorporated herein by reference in their entirety.

FIELD OF THE INVENTION

The present invention relates to a novel process for preparing amorphous (4R-cis)-6-[2-[3-phenyl-4-(phenylcarbamoyl)-2-(4-fluorophenyl)-5-(1-methylethyl)-pyrrol-1-yl]-ethyl]-2,2-dimethyl-[1,3]-dioxane-4-yl-acetic acid-tertiary butyl ester. This compound is useful as an intermediate in preparing atorvastatin salts.

TECHNICAL BACKGROUND

Atorvastatin is known pharmaceutical substance (Merck Index, 12$^{th}$ edition, 1996, No. 897), and has the chemical name hemi calcium salt (R-(R*,R*))-2-(4-fluorophenyl)-β,δ-dihydroxy-5-(1-methylethyl)-3-phenyl-4-((phenylamino)carbonyl)-1H-pyrrol-1-heptanoic acid. Atorvastatin may exist in free acid form as well as in acid salts form and in hydrates and solvates forms. Atorvastatin is also known as lactone form that may be prepared from free acid form. Solid atorvastatin salts exist in amorphous or crystalline form. Suitable salts of atorvastatin includes alkaline metal salts, earth alkaline metal salts, preferred for pharmaceutical use are earth alkaline salts, such as a calcium salt.

The compound (4R-cis)-6-[2-[3-phenyl-4-(phenylcarbamoyl)-2-(4-fluorophenyl)-5-(1-methylethyl)-pyrrol-1-yl]-ethyl]-2,2-dimethyl-[1,3]-dioxane-4-yl-acetic acid-tertiary butyl ester of the formula I

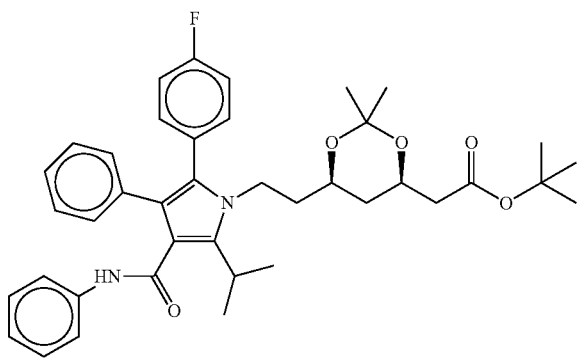

I was first described in EP 330172 and is known as an important intermediate for the preparation of atorvastain by using specific synthesis procedure. The patent EP 330172 discloses the preparation of (4R-cis)-6-[2-[3-phenyl-4-(phenylcarbamoyl)-2-(4-fluorophenyl)-5-(1-methylethyl)-pyrrol-1-yl]-ethyl]-2,2-dimethyl-[1,3]-dioxane-4-yl-acetic acid-tertiary butyl ester. Compound of the formula I was prepared by the convergent synthesis with a chain of reactions. The important last step includes reaction of (4R-cis)-1,1-dimethylethyl 6-(2-aminoethyl)-2,2-dimethyl-1,2-dioxane-4-acetate and 4-fluoro-α-[2-methyl-1-oxopropyl]-γ-oxo-N-,β-diphenyl-benzenebutaneamide (which includes mixture of all possible isomers) in a mixture of solvents that contains heptane and toluene. Reaction was carried out at reflux temperature followed by addition of 2-propanol and cooling. The product should be a yellow solid. The patent does not teach in which polymorphous form is the product and does not define the melting point of the product. When we tried to rework said procedure we obtained instead of yellow solid, slight yellow oily product that did not crystallize. We found out that the oily product was not pure and because of containing significant amount of impurities as such is not suitable for use in the preparation of atorvastatin salts. The purity was less than 70%, determined by HPLC analysis. Another patent that discloses the same process for the preparation of the compound of the formula I is U.S. Pat. No. 5,155,251 and rework of this procedure also gave oily impure product.

WO 03/024959 discloses new crystalline forms I and II of the compound of the formula I, and a process of preparation thereof. The application disclose the process that uses an organic solvents for the preparation of crystal polymorphs of compound shown in the formula I. E.g. in example 3 it is disclosed the use of acetonitrile for dissolving crude amorphous substance of the formula I and than heating the obtained mixture at the reflux temperature. Afterwards the mixture is cooled and allowed to stay overnight. The precipitate formed is filtered, washed and dried. The product obtained is in crystal form I.

Constantly there is a strong demand for pure and uniform products having physical properties appropriate for easily scaling-up procedure and use in industrial scale. Above mentioned prior art discloses processes for the preparation of the compound of the formula I. As said above synthesis process, disclosed in the EP 330172 and U.S. Pat. No. 5,155,251 for the preparation of the compound shown in the formula I is not reproducible as the product obtained is oily without tendency to crystallize. Oily products were impure and as such not favourable in the preparation of atorvastatin because the purity of end product atorvastatin depends on the purity of the starting compound. Crystallization processes from prior art WO 03/024959 provides crystal forms of the compound of the formula I that dissolves slowly in organic solvents and also may be impure.

It is very important that the atorvastatin producing starting compound of the formula I dissolves quickly and completely in aprotic solvents, e.g. tetrahydrofurane, because the first step in the synthesis of atorvastatin salts includes usually dissolving said starting compound in an aprotic solvent. The dissolving process should provide a clear solution as fast as possible and if this is not the case more solvent may be added and more time for stirring should be spent. Also if the obtained solution is not clear, filtering may be applied to minimize the impurities in the final product.

Crystalline products are generally less soluble (or they dissolve slowly due to the large crystals), and are from one aspect more difficult for purification in comparison to amorphous products. The reason for this is that a larger crystals in the crystalline product may incorporate a larger amount of impurities and residual solvents during the crystal formation. Therefore If some quantity of water, or maybe other solvents and impurities is incorporated in large crystals this water cannot be easily removed therefrom during a drying process. Also impurities incorporated inside the crystal cannot be washed out during the washing process, that is generally used after membrane filtration. Hence, if a compound of the formula I is dissolved for the reaction to prepare atorvastatin salts, said incorporated water and potential impurities also dissolves in the solvent and result in a mixture of water with the aprotic solvent used for dissolving the starting compound. A compound of the formula I has a very poor solubility in water or is practically insoluble in water. Therefore, the presence of water in the solvent for dissolving a compound of the formula I to prepare atorvastatin may result in a loss of starting compound because the portion of it that does not dissolve in the reaction mixture cannot react with reagents and may be lost during the reaction process by filtration. Higher volumes of the organic solvent which may be necessary to dissolve a compound of the formula I due to the presence of water, have to be recovered which will increase energy consumption.

A comparison between the solubility of amorphous and crystalline compound of the formula I shows that the amorphous substance is better soluble in aprotic organic solvents, such as for example ethers, such as diisopropyl ether, cyclic carbohydrates such as methyl cyclohexane, and lower alcohols (C1-C4 alcohols) such as isopropanol. In the case of tetrahydrofuran (THF) that is generally used as the solvent for dissolution of compound of the formula I in the synthesis of atorvastatin calcium it was found that some dimness appeared if crystal form of the pyrrole compound of the formula I was dissolved. However, a perfectly clear solution was obtained if amorphous compound of the formula I was dissolved in THF. If the solution as in the case mentioned above is not clear, further purification steps, e.g. by filtering and/or adding of active charcoal may become necessary to obtain a clear solution to be used for further reactions in order to avoid impurities in the final product such as atorvastatin calcium. Additional purification steps implicates increased reaction times and higher production costs.

If the oily impure substance of the formula I, obtained from processes disclosed in EP 330172 and U.S. Pat. No. 5,155,251 is used for the production of atorvastatin salts, in the first step which includes dissolution of compound of formula I in THF, impure reaction mixture resulted that should be purified before further procedure steps which includes filtration step and more time consumed and energy spend.

In said application WO03/024959 which discloses the processes for the preparation of crystal forms of the compound of the formula I, amorphous compound of the formula I is used as starting material but the patent application is silent on how this amorphous starting material is prepared.

The use of an amorphous form of a compound of the formula I in the synthesis of atorvastatin calcium has an advantage because of better solubility in aprotic organic solvents regarding crystall forms and increased purity compared with the use of a crystalline form containing very large crystalls or the impure oily product of a compound of the formula I.

DETAILED DESCRIPTION OF THE INVENTION

Figure 1:
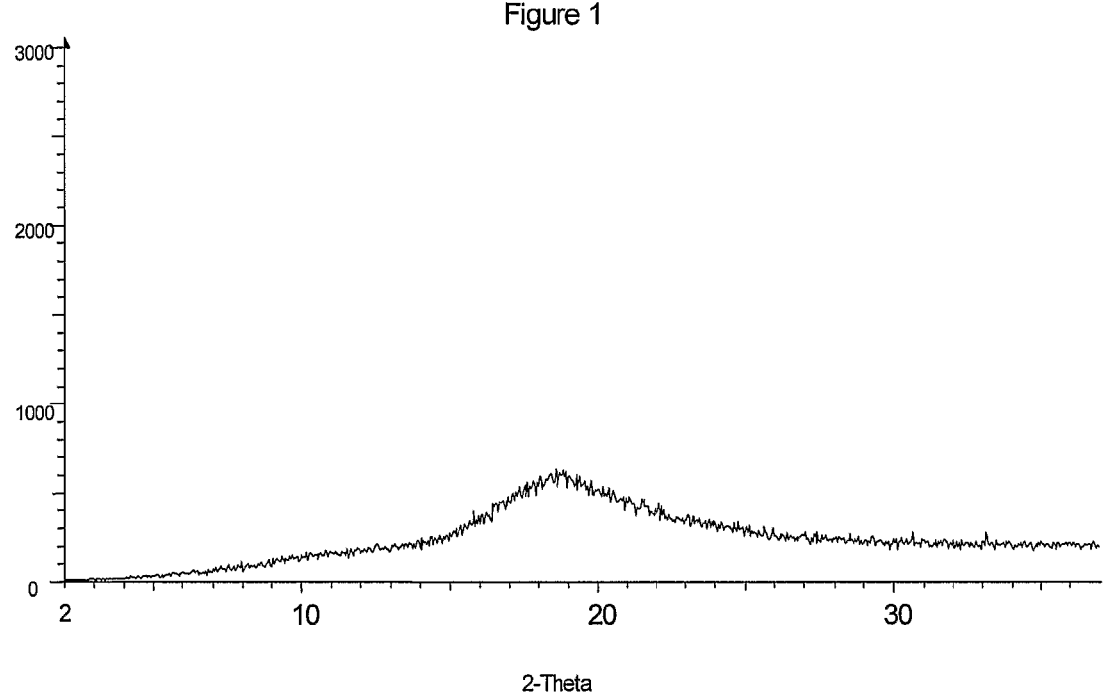
FIG. 1: An X-ray powder diffraction pattern of amorphous (4R-cis)-6-[2-[3-phenyl-4-(phenylcarbamoyl)-2-(4-fluorophenyl)-5-(1-methylethyl)-pyrrol-1-yl]-ethyl]-2,2-dimethyl-[1,3]-dioxane-4-yl-acetic acid-tertiary butyl ester (compound of the formula I) obtained from Example 4.

As mentioned above, there exists a constant need for preparing amorphous compound of the formula I because the processes for the preparation of atorvastatin salts demand pure and in organic solvents fast dissolving starting compound of the formula I which is a key intermediate in the synthesis of atorvastatin salts.

In a first aspect the present invention provides therefore a process for preparing amorphous compound of the formula I, that may be used for preparing amorphous atorvastatin calcium. The process of the present invention is simple and may therefore easily be scaled up to an industrial scale.

The purity of the oily products, obtained by processes disclosed in EP 330172 and U.S. Pat. No. 5,155,251 was low, as it was determined by HPLC at lower than 70% of HPLC purity. As we are talking about pure products, we understand that pure product means the degree of HPLC purity of at least 85%, preferably more than 95%, most preferably more than 99% of chromatographic purity determined by HPLC method. We prepared our amorphous product of the compound of the formula I by using methods here disclosed with more than 99% of HPLC purity.

In a second aspect the invention relates to a process of preparing amorphous compound of the formula I, by dissolving the compound of the formula I, having specific polymorphous form, which may be any crystalline form, such as crystalline form I or form II of the compound of the formula I as well as any form wherein the crystalline status cannot be determined, e.g. oily form or mixture of known polymorphous forms, in an organic solvent, selected from the group consisting of lower alkanols (C1 to C4 alkanoles) in which compound of the formula I dissolves well, e.g., methanol and concentrating the solution under normal or reduced pressure at room or increased temperature, temperature range should be from 25-100° C., preferably 30-60° C., most preferably at 50-60° C. until the solution is still absolutely clear, that means to the point when there is no dimness in the solution. Thereafter, water is added to the solution to produce a precipitate of amorphous compound of the formula I, which is filtered and optionally dried. Drying is carried out according to known conventional drying methods, e.g. at room temperature or increased temperature of up to 60° C. and under normal or reduced pressure such as from 1 to 50 mbar. The obtained residue is amorphous compound of the formula I. The HPLC purity determined for the product is more than 99%.

A further aspect of the present invention concerns a process of preparing amorphous compound of the formula I by dissolving crystalline compound of the formula I in an inert organic solvent, selected from the group consisting of lower alkanoles e.g. methanol, chlorinated lower alkanes, e.g. chloroform and methylene chloride, ketones such as acetone, aromatic hydrocarbons such as benzene and toluene, cyclic ethers such as tetrahydrofuran and nitrites such as acetonitrile, at room or increased temperature up to 60° C. The amount of solvent is not critical but should be high enough to produce a completely clear solution. Then the solvent is evaporated off under normal or reduced pressure, reduced pressure scale should be from 1-5 mbar, at room or increased temperature, the temperature range should be from 25-100° C., preferably 30-60° C., most preferably at 50-60° C., to completely remove the solvent from the mixture. Thereafter the residue is optionally dried. Drying is carried out according to known conventional drying methods, e.g. at room temperature or increased temperature of up to 60° C. and under normal or reduced pressure such as from 1 to 50 mbar. The obtained residue is amorphous compound of the formula I. The HPLC purity determined for the product is more than 99%.

The following non-limiting Examples illustrate the present invention without limiting the scope of the invention to said Examples.

Preparation of amorphous (4R-cis)-6-[2-[3-phenyl-4-(phenylcarbamoyl)-2-(4-fluorophenyl)-5-(1-methylethyl)-pyrrol-1-yl]-ethyl]-2,2-dimethyl-[1,3]-dioxane-4-yl-acetic acid-tertiary butyl ester (compound of the formula I).

Example 1

5 g of the compound of the formula I are dissolved in 100 ml of methanol. The clear solution is concentrated at reduced pressure of 2 mbar to a point where the solution is still totally clear, i.e. to a volume of approximately 20 ml. Then 200 ml of water are added and an amorphous residue precipitates. The precipitate is filtered off and dried at reduced pressure of 50 mbar at 60° C. for 5 hours. The yield of amorphous compound of the formula I is 4.46 g.

Example 2

5 g of the compound of the formula I are dissolved in 100 ml of acetonitrile to obtain the clear solution. The solution is dried at reduced pressure of 2 mbar at 60° C. until a completely dry product is obtained. The yield of amorphous compound of the formula I is 5 g.

Example 3

5 g of the compound of the formula I are dissolved in 10 ml of methylene chloride. The obtained clear solution is dried at reduced pressure of 2 mbar at 60° C. until a completely dry product is obtained. The yield of amorphous compound of the formula I is 5 g. The HPLC purity of the obtained product is 99.4%.

Example 4

5 g of the compound of the formula I are dissolved in 5 ml of chloroform. The clear solution is allowed to stand without a cover at room temperature long enough (several hours) to completely evaporate solvent from the material. After that the residue is dried at reduced pressure of 50 mbar for 5 hours at 50° C. The yield of the amorphous compound of the formula I is 5 g.

Example 5

5 g of the compound of the formula I are dissolved in 5 ml of chloroform. The obtained clear solution is dried at reduced pressure of 2 mbar at 60° C. until a completely dry product is obtained. The yield of amorphous compound of the formula I is 5 g.

Example 6

X-Ray Powder Diffraction Analysis of Amorphous Compound of the Formula I

Amorphous compound of the formula I obtained from Example 4 has an X-ray powder diffraction pattern substantially as shown in FIG. 1.

The X-ray powder diffraction pattern is measured with a Philips PW1710 difractometer in reflection geometry. The instrument is regularly calibrated with a silicon standard. A standard Philips back-loading sample holder is used. Sample storage, mounting, and data collection are performed at room temperature. Instrumental parameters are: $CuK_\alpha$ radiation (30 mA, 40 kV, $\lambda$=1.5406 Å, variable divergence slit (approx. 12×16 mm irradiated area), 0.4 mm receiving slit, graphite monochromator on the secondary side, scintillation counter. Data collection parameters are: 2θ range from 4° to 37°, step scan mode in steps of 0.04° 2θ, integration time 1 second at each step.

Example 7

DSC Analysis of Amorphous Compound of the Formula I

Figure 2:
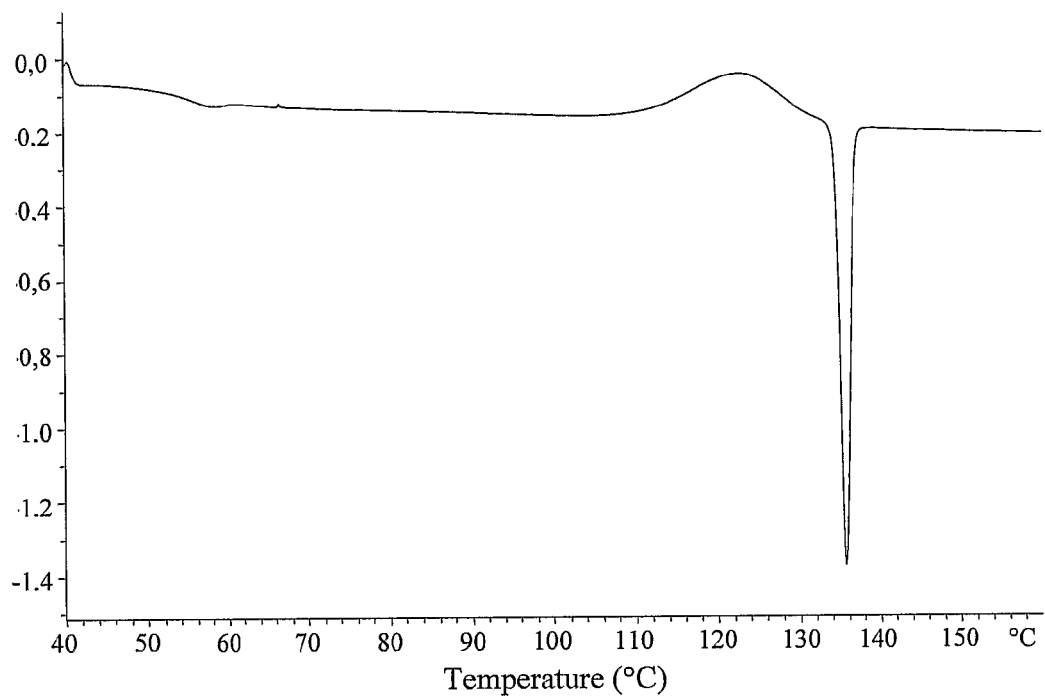
FIG. 2: DSC thermogram of amorphous compound of the formula I obtained from Example 2.

The DSC (Differential Scanning Calorimetry) analysis is performed on an Mettler Toledo DSC822e analyzer. Measurement is performed in an unsealed Al pan with a heating rate of 5 K/min. The heating interval is 40-160° C. The thermogram of amorphous compound of the formula I prepared by Example 2 is expressed in FIG. 2.

The DSC curve shows the thermal transformation of amorphous compound of the formula I into crystalline forms. In the DSC curve there is clearly seen the formation of crystals of Form II at around 120° C. and melting point of these crystals at 136° C.

The invention claimed is:

1. A process for the preparation of amorphous (4R-cis)-6-[2-[3-phenyl-4-(phenylcarbamoyl)-2-(4-fluorophenyl)-5-(1-methylethyl)-pyrrol-1-yl]-ethyl]-2,2-dimethyl-[1,3]-dioxane-4-yl-acetic-acid-tertiary butyl ester, which comprises:
   a) dissolving crystalline (4R-cis)-6-[2-[3-phenyl-4-(phenylcarbamoyl)-2-(4-fluorophenyl)-5-(1-methylethyl)-pyrrol-1-yl]-ethyl]-2,2-dimethyl-[1,3]-dioxane-4-yl-acetic-acid-tertiary butyl ester in an inert organic solvent,
   b) concentrating the solution,
   c) adding water,
   d) precipitating the amorphous product,
   e) optionally isolating the precipitated product to obtain amorphous (4R-cis)-6-[2-[3-phenyl-4-(phenylcarbamoyl)-2-(4-fluorophenyl)-5-(1-methylethyl)-pyrrol-1-yl]-ethyl]-2,2-dimethyl-[1,3]-dioxane-4-yl-acetic-acid-tertiary butyl ester.

2. The process according to claim 1, wherein the organic solvent is selected from the group of lower $C_1$-$C_4$ alkanols.

3. The process according to claim 1, wherein the organic solvent is methanol.

4. The process according to claim 1, wherein the concentration of the solution is performed at reduced pressure to a point where the solution is clear.

5. The process according to claim 1, wherein the crystalline (4R-cis)-6-[2-[3-phenyl-4-(phenylcarbamoyl)-2-(4-fluorophenyl)-5-(1-methylethyl)-pyrrol-1-yl]-ethyl]-2,2-dimethyl-[1,3]-dioxane-4-yl-acetic-acid-tertiary butyl ester is crystalline form I.

6. The process according to claim 1, wherein the crystalline (4R-cis)-6-[2-[3-phenyl-4-(phenylcarbamoyl)-2-(4-fluorophenyl)-5-(1-methylethyl)-pyrrol-1-yl]-ethyl]-2,2-dimethyl-[1,3]-dioxane-4-yl-acetic-acid-tertiary butyl ester is crystalline form II.

* * * * *